(12) United States Patent
Kajino et al.

(10) Patent No.: US 6,783,755 B2
(45) Date of Patent: Aug. 31, 2004

(54) TOPICAL COMPOSITIONS

(75) Inventors: Takayoshi Kajino, Tokyo (JP); Takeshi Ihara, Wakayama (JP); Hisakazu Furugaki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/458,227

(22) Filed: Jun. 11, 2003

(65) Prior Publication Data

US 2003/0232026 A1 Dec. 18, 2003

(30) Foreign Application Priority Data

Jun. 12, 2002 (JP) ........................................ 2002-171701
Apr. 16, 2003 (JP) ........................................ 2003-111191

(51) Int. Cl.$^7$ .............................. A61K 7/34; A61K 7/38
(52) U.S. Cl. .......................................... 424/66; 424/68
(58) Field of Search ............................. 424/68, 70, 66, 424/65, 70.4

(56) References Cited

U.S. PATENT DOCUMENTS

| | | | | |
|---|---|---|---|---|
| 4,724,139 A | * | 2/1988 | Palinczar | 424/66 |
| 5,124,361 A | | 6/1992 | Fukasawa et al. | |
| 5,202,123 A | * | 4/1993 | Katsoulis | 424/401 |
| 5,972,319 A | * | 10/1999 | Linn et al. | 424/65 |
| 6,403,070 B1 | * | 6/2002 | Pataut et al. | 424/65 |
| 2002/0119109 A1 | * | 8/2002 | Herpens et al. | 424/68 |

FOREIGN PATENT DOCUMENTS

| | | |
|---|---|---|
| JP | 01-193278 | 8/1989 |
| JP | 07-506833 | 7/1995 |
| JP | 09-157147 | 6/1997 |
| WO | WO 93/23008 | 11/1993 |

* cited by examiner

Primary Examiner—Raymond J. Henley, III
(74) Attorney, Agent, or Firm—Oblon, Spivak, McClelland, Maier & Neustadt, P.C.

(57) ABSTRACT

Provided is a topical composition containing phosphate(s), its salts, and mixtures thereof, represented by the following formula(s) (1) and (2):

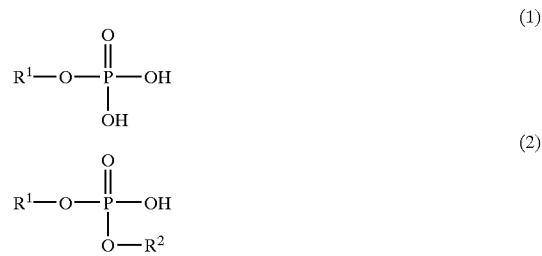

(wherein, $R^1$ and $R^2$ each represent a linear or branched hydrocarbon group having 8 to 36 carbon atoms). The topical composition further contains a zirconium salt, an aluminum zirconium complex salt, and mixtures thereof. In preferred embodiments of the present invention, the topical composition can have an antiperspirant action, be excellent in the feel during or after their application to the skin, and leaving mostly no white residue on the skin.

11 Claims, No Drawings

TOPICAL COMPOSITIONS

BACKGROUND OF THE INVENTION

1. Field of the invention

The present invention relates to improved topical compositions containing inorganic metal compounds.

2. Background Art

Cosmetic compositions for inhibiting perspiration in hot and humid weather or preventing an axillary odor due to perspiration have conventionally contained, as an antiperspirant, an inorganic metal compound having an astringent action on the skin. For example, aluminum chloride, aluminum hydroxychloride, zirconium hydroxychloride, zinc chloride, zinc sulfate or the like have been incorporated. Such cosmetic compositions have been supplied in forms such as a lotion, emulsion, spray, gel, gel stick and the like.

Among them, a gel stick type composition containing a gelling agent consisting of an n-acyl amino acid amide and 12-hydroxystearic acid, an oily substance and an antiperspirant as described above has been proposed (International Patent Publication No. Hei 7-506833; WO93/23008). Incorporation of a conventionally employed antiperspirant in a gel composition, however, involves problems wherein a whitening (i.e. white residue) appears on the dried skin, for example, the underarm skin to which the composition has been topically applied to, impairing the appearance and feeling upon use.

On the other hand, a dialkylphosphate polyaluminum salt available by reacting a dialkylphosphate (or salt thereof) with a basic polyaluminum salt has been proposed as an oil gelling agent (Japanese Patent Laid-Open No. Hei 1-193278; U.S. Pat. No. 5,124,361). Application examples of it to topical compositions such as antiperspirant cosmetic compositions are however not disclosed.

An antiperspirant spray composition comprising an antiperspirant, a phosphoric acid type anionic surfactant such as polyoxyethylene alkyl ether phosphoric acid, an oil, silicic acid anhydride, ethyl alcohol and a propellant has also been proposed (Japanese Patent Laid-Open No. Hei 9-157147). The compositions disclosed therein however relates to a powder spray.

SUMMARY OF THE INVENTION

The present invention relates to a composition containing a specific phosphate or salt thereof (including its mixtures), together with a zirconium salt and/or an aluminum zirconium complex salt.

According to the present invention, there is thus provided a topical composition, which comprises a phosphate(s) represented by the following formula(s) (1) and/or (2):

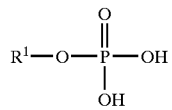

(1)

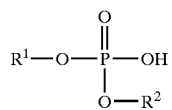

(2)

(wherein, $R^1$ and $R^2$ each represents a linear or branched hydrocarbon group having 8 to 36 carbon atoms) or a salt thereof, and a zirconium salt and/or aluminum zirconium complex salt.

DETAILED DESCRIPTION OF THE INVENTION

All publications cited herein are incorporated by reference.

The phosphate to be used as Component (A) in the present invention is a phosphate ester, its salts, and mixtures thereof represented by formula (1) and formula (2). A phosphate monoester is represented by formula (1) and a phosphate diester is represented by formula (2). The hydrocarbon group represented by $R^1$ or $R^2$ in the formulas may be any hydrocarbon group which is saturated or unsaturated, and linear or branched insofar as it has 8 to 36 carbon atoms. Particularly preferred from the viewpoint of gelling capacity to form a gel composition are saturated hydrocarbon groups, more preferably saturated and branched hydrocarbon groups. $R^1$ and $R^2$ may be the same or different.

Specific examples of such hydrocarbon groups include octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, decenyl, dodecenyl, undecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, octadienyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadienyl, 2-hexyldecyl, 2-octylundecyl, 2-decyltetradecyl, eicosadecyl, 2-ethylhexyl, 1,1,3,3-tetramethylbutyl, 3,7-dimethyloctyl, 3,7-dimethyloctan-3-yl, 2-hexyldecyl, 2-heptylundecyl, 2-octyldodecyl, 3,7,11-trimethyldodecyl, 3,7,11,15-tetramethylhexadecyl, 3,5,5-trimethylhexyl, 2,3,4-trimethylpentan-3-yl, 2,3,4,6,6-pentamethylheptan-3-yl, isostearyl, 2-decyltetradecyl, 2-dodecylhexadecyl, 2-tetradecyloctadecyl and 2-hexadecyleicosadecyl groups.

Among them, saturated branched hydrocarbon groups having 12 to 24 carbon atoms are particularly preferred.

These phosphates may be used in the acid form, but are usable as salts such as salts of an alkali metal such as sodium, potassium, or the like, salts of an alkanolamine such as monoethanolamine, diethanolamine, triethanolamine, or the like, or salts of a basic amino acid such as lysine, arginine, or the like. Phosphates in the acid form are economically preferred because they can be prepared at a lower cost.

As Component (A), the phosphate containing a phosphate monoester (1) and a phosphate diester (2) in combination is preferred. The phosphate containing the monoester and diester in a (1):(2) ratio (weight ratio) ranging from 90:10 to 0.1:99.9, especially from 60:40 to 1:99 is preferred, because it exhibits good gel forming capacity.

The phosphate as Component (A) is available by reacting the corresponding aliphatic alcohol with a phosphorylating reagent such as diphosphorus pentaoxide, phosphorus oxychloride, or the like under conditions permitting formation of the monoester (1) and diester (2) in a desired ratio; and then neutralizing the reaction product as needed. The reaction product contains a small amount of triester, unreacted alcohol and the like, though depending on the nature of the raw materials and reaction conditions. Such triester and the like have less influence on the properties intended in the present invention.

As Component (A), one or more phosphates or salts thereof are usable. The addition of them in an amount of 3 to 10 wt. %, especially 4 to 8 wt. % based on the total composition is preferred in order to impart the resulting composition with excellent feeling upon use.

The zirconium salt or aluminum zirconium complex salt as Component (B) is a salt conventionally employed as an antiperspirant. Examples of the zirconium salt include zirconium chloride, zirconium hydroxychloride and zirconium compounds represented by the following formula (3):

$$ZrO(OH)_{2-my}X_y \qquad (3)$$

(wherein, X represents a halogen atom, nitrate ion, sulfate ion or sulfamate ion, y represents a number from 0.9 to 2, m represents a valence of X and 2-my represents a number of not less than 0).

Examples of the aluminum zirconium complex salt include aluminum zirconium chloride, aluminum zirconium chlorohydroxide, aluminum zirconium glycine complex, and aluminum zirconium propylene glycol complex.

As Component (B), commercially available products are also usable. Aluminum zirconium propylene glycol complexes include "REZAL® 36 GPG Powder", "REACH® AZP-908 PG Powder" (each, product of Reheis, Inc.), and "Westchlor® ZR41 PG ASP Powder (product of Westwood Chemical), while aluminum zirconium glycine complexes include "REACH® AZP-908", "REACH® AZP-908SUF", and "REACH® AZP-902" (each, product of Reheis, Inc.).

As Component (B), at least one of the compounds as described above is usable. Addition of the compound in an amount of 10 to 30 wt. %, especially 15 to 25 wt. % based on the total amount of the composition is preferred, because it brings about a high perspiration inhibiting effect and excellent feeling upon use. Addition of the compound in an amount exceeding the above range tends to deteriorate the feeling upon use.

The topical composition according to the present invention can be prepared by mixing, in an appropriate medium, Components (A) and (B) with the other components which will be described below. As the medium, an aqueous medium described below or a mixture thereof with a non-aqueous medium is usable. It is presumed that the zirconium salt or aluminum zirconium complex salt of a phosphate is formed in the composition thus prepared. Although it is possible to prepare the zirconium salt or aluminum zirconium complex salt of the phosphate in advance, and then incorporate it in the aimed topical composition, a process of directly adding Components (A) and (B) to a composition, thereby preparing the topical composition is more advantageous than the former process in view of convenience.

The aluminum zirconium complex salt of the phosphate is a novel compound.

Such a compound is available by reacting Components (A) and (B) in an appropriate medium. In one such case, the phosphate (1) and/or (2), or salt thereof is mixed and reacted with 0.01 to 1.1 equivalents of a zirconium salt and/or aluminum zirconium complex salt in an aqueous medium or a mixture of an aqueous medium with a non-aqueous medium. The reaction is effected at 10 to 90° C., preferably 20 to 80° C., for 0.5 to 8 hours. When a precipitate appears after completion of the reaction, it is filtered off. The solvent is also distilled off under reduced pressure to obtain the intended compound. The compound may be washed if necessary.

Examples of the aqueous medium usable here include water, methanol, ethanol, acetone, and isopropyl alcohol. They may be used either singly or in combination.

Examples of the non-aqueous medium include hexane, octane, decane, dodecane, isoparaffin, toluene, terpenes, cyclic or linear silicone oils.

As a mixed medium, a mixture of one aqueous medium and one non-aqueous medium or a mixture of a plurality of aqueous media and a plurality of non-aqueous media may be used.

The topical composition according to the present invention may further contain component (C), a liquid oil. The liquid oil is in liquid form at 25° C. and may be either volatile or nonvolatile. Examples include hydrocarbons such as decane, dodecane, liquid paraffin, liquid isoparaffin, light liquid isoparaffin, mineral oil, squalane and squalene; eucalyptus oil, peppermint oil, camellia oil, Macadamia nut oil, avocado oil, yolk oil, olive oil, lanolin and jojoba oil; ester oils such as glycerol monooleate, isopropyl palmitate, isopropyl stearate, butyl stearate, isopropyl myristate, neopentyl glycol dicaprylate, diethyl phthalate, myristyl lactate, diisopropyl adipate, 2-ethylhexyl palmitate, 2-octyldodecyl myristate, neopentyl glycol di-2-ethylhexanoate, 2-octyldodecyl oleate and glycerol triisostearate; higher fatty acids such as isostearic acid and oleic acid; and silicone oils.

In the present invention, silicone oils ordinarily added to topical compositions are usable. Examples include dimethylpolysiloxane, high-polymerization-degree dimethylpolysiloxane, and methylphenylpolysiloxane; and cyclic dimethylpolysiloxanes such as octamethylcyclotetrasiloxane and decamethylcyclopentasiloxane.

As the liquid oil, one or more of the above-described ones are usable. They are preferably added in an amount of 20 to 80 wt. %, especially 30 to 70 wt. % based on the total amount of the composition.

In the present invention, addition of such a liquid oil facilitates preparation of a thixotropic soft gel and thus its use is suited for obtaining a gel cosmetic composition.

The topical composition according to the present invention may further contain a solid fat, water, various surfactants, a humectant, an antiseptic, an antioxidant, a pharmaceutically effective ingredient, a perfume, a powder and the like.

The topical composition according to the present invention can be prepared, for example, by mixing an oil phase containing Component (A) and an aqueous solution of Component (B) while stirring and heating at 40° C. to 80° C.

The topical composition according to the present invention is usable as any one of a pharmaceutical and/or a cosmetic and it is particularly useful as an antiperspirant product or antiperspirant cosmetic composition.

The following examples further describe and demonstrate embodiments of the present invention. The examples are given solely for the purpose of illustration and are not to be construed as limitations of the present invention.

EXAMPLES

Preparation Example 1

Dihexadecylphosphate (monoester:diester=2:98 (molar ratio)) (25.2 g) and 62.8 g of ethanol were mixed to dissolve the former in the latter. To the resulting solution was added 63.9 g of a 3 wt. % aqueous solution of sodium hydroxide, followed by the dropwise addition of 26.2 g of a 30 wt. % aqueous solution of aluminum zirconium glycine complex ("REACH® AZP-908SUF", product of Reheis, Inc.) over 1 hour while stirring at 60° C. After completion of the dropwise addition, the reaction mixture was aged at 65° C. for 4 hours. After completion of the reaction, the resulting solid was collected by filtration, washed successively with deionized water (125 g×1) and ethanol (125 g×3), and dried at room temperature under reduced pressure, whereby 26.6 g of aluminum zirconium dihexadecylphosphate was obtained as a white powder.

Preparation Example 2

Didodecylphosphate (monoester:diester=5:95 (molar ratio)) (13.1 g) and 32.9 g of ethanol were mixed to dissolve the former in the latter. To the resulting solution was added 40.5 g of a 3 wt. % aqueous solution of sodium hydroxide, followed by the dropwise addition of 17.0 g of a 30 wt. % aqueous solution of aluminum zirconium glycine complex ("REACH® AZP-908SUF", product of Reheis, Inc.) over 1 hour while stirring at 60° C. After completion of the dropwise addition, the reaction mixture was aged at 65° C. for 4 hours. After completion of the reaction, the resulting solid was collected by filtration, washed successively with deionized water (66 g×1) and ethanol (66 g×3), and dried at room temperature under reduced pressure, whereby 13.9 g of aluminum zirconium didodecylphosphate was obtained as a white powder.

Preparation Example 3

Diisostearylphosphate (monoester:diester=5:95 (molar ratio)) (30.4 g) and 76.5 g of ethanol were mixed to dissolve the former in the latter. To the resulting solution was added 49.4 g of a 3 wt. % aqueous solution of sodium hydroxide, followed by the dropwise addition of 21.3 g of a 30 wt. % aqueous solution of aluminum zirconium glycine complex ("REACH® AZP-908SUF", product of Reheis, Inc.) over 1 hour while stirring at 60° C. After completion of the dropwise addition, the reaction mixture was aged at 62° C. for 4 hours. After completion of the reaction, 200 mL of hexane and 200 mL of ethanol were added to cause phase separation of the mixture. The hexane layer thus separated was washed with deionized water (100 mL×2). The hexane layer was collected, to which 1000 mL of acetone was added. The resulting solid was collected and washed twice with 1000 mL of acetone. The solid thus obtained was dried at room temperature under reduced pressure, whereby 19.0 g of aluminum zirconium diisostearylphosphate was obtained as a white powder.

Preparation Example 4

Aluminum zirconium glycine complex ("REACH® AZP-908SUF", product of Reheis, Inc.) (12.5 g), 20 mL of deionized water and 50 mL of ethanol were mixed. To the solution thus obtained were added 2.5 g of diisostearylphosphate (monoester:diester=5:95 (molar ratio)) and 50 mL of ethanol. After mixing, the resulting mixture was aged at 60° C. for 2 hours. After completion of the reaction, the solvent was distilled off under reduced pressure, whereby 14.2 g of aluminum zirconium diisostearylphosphate was obtained as a white powder.

Preparation Example 5

Aluminum zirconium glycine complex ("REACH® AZP-908SUF", product of Reheis, Inc.) (12.5 g), 20 mL of deionized water and 50 mL of ethanol were mixed. To the solution thus obtained were added 2.5 g of isostearylphosphate (monoester:diester=52:48 (molar ratio)) and 50 mL of ethanol. After mixing, the resulting mixture was aged at 60° C. for 2 hours. After completion of the reaction, the solvent was distilled off under reduced pressure, whereby 14.2 g of aluminum zirconium isostearylphosphate was obtained as a white powder.

Preparation Example 6

(1) After 1028.8 g of isostearyl alcohol and 257.2 g of 2-decyltetradecyl alcohol were mixed, 214 g of diphosphorus pentaoxide was added. The resulting mixture was heated and the mixture was aged at 80° C. for 15 hours. After aging, 150 g of deionized water was added and the mixture was stirred at 85° C. for 4 hours. After completion of the reaction, deionized water was distilled off under reduced pressure to obtain 1470 g of isostearyl-2-decyltetradecylphosphate (monoester:diester=52:48 (molar ratio)). The triester in the reaction product was below the detection limit. This also holds true for the above-described phosphates obtained in Preparation Examples 1 to 5.

(2) Aluminum zirconium glycine complex ("REACH® AZP-908SUF", product of Reheis, Inc.) (12.5 g), 20 ml of deionized water and 50 mL of ethanol were mixed. To the resulting solution were added 2.5 g of the isostearyl-2-decyltetradecylphosphate obtained in (1) and 50 mL of ethanol. After mixing, the mixture was aged at 60° C. for 2 hours. After completion of the reaction, the solvent was distilled off under reduced pressure to obtain 14.5 g of aluminum zirconium isostearyl-2-decyltetradecylphosphate as a white powder.

Example 1

Gel topical compositions as shown in Table 1 were prepared and antiperspirant effects, feeling and the amount of white residue remaining after application to the skin were evaluated. The results are also shown in Table 1. In the table, DAP and MAP represents a dialkyl phosphate and a monoalkyl phosphate, respectively.

Preparation Process

An oil phase containing Component (A) and a liquid oil, and an aqueous solution of Component (B) in deionized water as shown in Table 1, each heated to 60° C., were mixed, followed by heating while stirring for 10 minutes, whereby a gel topical composition was obtained.

Evaluation Method

An appropriate amount of each composition was applied to the skin of a panel of 10 experts under the conditions of 38° C. and 40% RH. Thirty minutes later, its antiperspirant effect, feel on the skin during and after application and the amount of white residue of each composition was organoleptically evaluated. According to the criteria described below, the composition was evaluated and was rated based on its average score.

| (1) Antiperspirant effect | |
|---|---|
| Not sticky | Score 4 |
| Not so sticky | Score 3 |
| Somewhat sticky | Score 2 |
| Sticky | Score 1 |
| (2) Feel on the skin | |
| Very good | Score 4 |
| Good | Score 3 |
| Not very good | Score 2 |
| Bad | Score 1 |
| (3) White residue | |
| Very little residue | Score 4 |
| Little residue | Score 3 |
| Some residue | Score 2 |
| A lot of residue | Score 1 |

Criteria:
 A: average score: 3.5 to 4.0
 B: average score: 2.5 to 3.4
 C: average score: 1.5 to 2.4
 D: average score: 1.0 to 1.4

TABLE 1

| Component (wt. %) | | Preferred Embodiments of the Invention product | | | | | | | | | | | | | Comparative Product | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 1 | 2 |
| A | Isostearylphosphate (DAP:MAP = 50:44)*1 | 4 | | 7 | 8 | 5 | 6 | 4 | | 5 | 3 | 6 | 6 | 9 | | |
| | Isostearyl-2-decyltetradecylphosphate (DAP:MAP = 51:42)*1 | | 5 | | | | | | 10 | | | | | | | |
| B | Aluminum zirconium complex salt | 20 | | | | | | | | | | | | | 20 | 20 |
| | "REZAL ® 36 GPG Powder" (product of Reheis, Inc.) | | | | | | | | | | | | | | | |
| | "REACH ® AZP-908 PG Powder" (product of Reheis, Inc.) | | 25 | | | | | | | | | | | | | |
| | "Westchlor ® ZR41 PG ASP Powder" (product of Westwood Chemical Corp.) | | | | | 20 | | | | | | | | | | |
| | "REACH ® AZP-908" (product of Reheis, Inc.) | | | 24 | 24 | | 24 | | | 25 | 30 | | 24 | 24 | | |
| | "REACH ® AZP-902" (product of Reheis, Inc.) | | | | | | | 25 | 15 | | | 24 | | | | |
| | Deionized water | 15 | 20 | 24 | 24 | 17 | 24 | 25 | 10 | 30 | 40 | 50 | 24 | 24 | 20 | 45 |
| Liquid oil | Isostearic acid | | | | | | | | | | | | | | 5 | |
| | Dimethicone copolyol ("Silicone SH-3775M", product of Dow Corning Toray Silicone Co., Ltd.) | | | | | | | | | | | | | | | 10 |
| | Dipropylene glycol | | | | | | | | | | | | | | | 20 |
| | Decamethylcyclopentasiloxane ("Silicone SH-245", product of Dow Corning Toray Silicone Co., Ltd.) | 42 | 35 | 28 | 28 | 41 | 30 | 23 | 39 | 26 | 19 | 10 | 25 | 24 | 39 | 5 |
| | Liquid isoparaffin ("Polysynlane ®" product of NOF Corporation) | 19 | | 5 | | | 16 | | 26 | 14 | 8 | | | | 16 | |
| | Liquid paraffin ("Blanda ®" product of WITCO) | | 15 | | | 17 | | 23 | | | | 10 | | 5 | | |
| | Light liquid isoparaffin ("Isosol ® 400", product of Nippon Petrochemicals Co., Ltd.) | | | 12 | 16 | | | | | | | | 21 | 14 | | |
| Antiperspirant effect | | A | A | A | A | A | A | A | A | A | A | A | A | A | A | A |
| Feeling of the skin | | A | A | A | A | A | A | A | A | A | A | A | A | A | C | D |
| White residue | | A | A | A | A | A | A | A | A | A | A | A | A | A | D | D |

*1: weight ratio. Unreacted alcohol, triester and the like constitute the remaining portion.

What is claimed is:

1. A topical composition comprising:
a phosphate salt formed by mixing component (A) and component (B)
wherein Component (A) is selected from the group consisting of phosphate(s), its salts, and mixtures thereof which are represented by the following formulas (1), and (2),

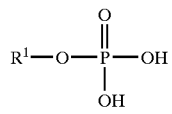  (1)

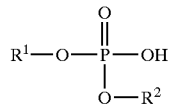  (2)

wherein, $R^1$ and $R^2$ each represents a linear or branched hydrocarbon group having 8 to 36 carbon atoms, and Component (B) is selected from the group consisting of a zirconium salt, an aluminum zirconium complex salt, and mixtures thereof.

2. The topical composition of claim 1, wherein in the formulas (1) and (2), $R^1$ and $R^2$ each represents a saturated hydrocarbon group.

3. The topical composition of claim 1 or 2, wherein in the formulas (1) and (2), $R^1$ and $R^2$ each represents a branched hydrocarbon group.

4. The topical composition of claim 1, wherein the composition comprises formula (1) and formula (2) in a (1):(2) weight ratio of 90:10 to 0.1:99.9.

5. The topical composition of claim 1, wherein Component (B) is a zirconium salt selected from the group consisting of zirconium chloride, zirconium chlorohydroxide, a zirconium compound represented by the following formula (3), $$ZrO(OH)_{2-my}X_y \qquad (3)$$

wherein, X represents a halogen atom, a nitrate ion, a sulfate ion or a sulfamate ion, y represents a number from 0.9; to 2, m represents a valence of X and 2-my represents a number of not less than 0, and mixtures thereof.

6. The topical composition of claim 1, wherein Component (B) is an aluminum zirconium complex salt selected from the group consisting of aluminum zirconium chloride, aluminum zirconium chlorohydroxide, aluminum zirconium glycine complex, aluminum zirconium propylene glycol complex, and mixtures thereof.

7. The topical composition of claim 1, further comprising Component (C) which is a liquid oil.

8. The topical composition of claim 1, wherein the composition is an antiperspirant cosmetic composition.

9. The topical composition of claim 1 comprising 3 to 10 wt. % of Component (A) and 10 to 30 wt. % of Component (B).

10. The topical composition of claim 7 comprising 20 to 80 wt. % of Component (C).

11. The topical composition of claim 7, wherein the composition is a gel cosmetic composition.

* * * * *